(12) United States Patent
Zhang et al.

(10) Patent No.: US 6,646,753 B2
(45) Date of Patent: Nov. 11, 2003

(54) IN-SITU THICKNESS AND REFRACTIVE INDEX MONITORING AND CONTROL SYSTEM FOR THIN FILM DEPOSITION

(75) Inventors: Jian Zhang, Brookline, MA (US); Jing Pan, Nashua, NH (US)

(73) Assignee: Unaxis, USA, Inc., St. Petersburg, FL (US)

( * ) Notice: Subject to any disclaimer, the term of this patent is extended or adjusted under 35 U.S.C. 154(b) by 46 days.

(21) Appl. No.: 09/971,374

(22) Filed: Oct. 4, 2001

(65) Prior Publication Data

US 2002/0075486 A1 Jun. 20, 2002

Related U.S. Application Data

(60) Provisional application No. 60/237,999, filed on Oct. 5, 2000.

(51) Int. Cl.$^7$ ............................................... G01B 11/06
(52) U.S. Cl. ........................ 356/632; 356/630; 356/503
(58) Field of Search ............................. 356/632, 503, 356/485, 504, 630; 250/559.27

(56) References Cited

U.S. PATENT DOCUMENTS

| | | |
|---|---|---|
| 4,748,329 A | 5/1988 | Cielo et al. |
| 4,878,755 A | 11/1989 | Siegmund et al. ............ 356/382 |
| 5,185,645 A | 2/1993 | Sartorius et al. |
| 5,619,329 A | 4/1997 | Otani ............................ 356/382 |
| 5,798,837 A | * 8/1998 | Aspnes et al. ................ 356/369 |
| 6,039,806 A | 3/2000 | Zhou et al. ................... 118/665 |

* cited by examiner

Primary Examiner—Richard A. Rosenberger
Assistant Examiner—Vincent Barth
(74) Attorney, Agent, or Firm—Kurt Rauschenbach; Rauschenbach Patent Law Group, LLC (57) ABSTRACT

A method of determining thickness and refractive index of an optical thin film is described. The method includes generating a diagnostic light beam having a first and a second wavelength. The method also includes measuring unattenuated light intensities at the first and the second wavelength of the diagnostic light beam. The method also includes measuring attenuated light intensities at the first and the second wavelength of the diagnostic light beam after transmission through the optical thin film. A null light intensity for the diagnostic light beam at the first and second wavelength is also determined. A first and second normalized intensity function is determined using the measured unattenuated light intensities, the measured attenuated light intensities, and the measured null light intensities. The thickness and refractive index of the optical thin film is then determined by solving the first and second normalized intensity function for thickness and refractive index.

29 Claims, 5 Drawing Sheets

IN-SITU THICKNESS AND REFRACTIVE INDEX MONITORING AND CONTROL SYSTEM FOR THIN FILM DEPOSITION

RELATED APPLICATIONS

This application claims the benefit of U.S. Provisional Application Ser. No. 60/237,999, filed Oct. 5, 2000, the entire disclosure of which is incorporated herein by reference.

FIELD OF THE INVENTION

The present invention relates to thickness and refractive index monitoring and control systems for thin film deposition. In particular, the present invention relates to methods and apparatus for in-situ monitoring and control of deposition rate, film thickness and refractive index of thin films.

BACKGROUND OF THE INVENTION

Many optical elements require optical thin film coatings. Optical coatings are deposited by a variety of techniques including evaporation, magnetron sputtering, and ion beam deposition. There are many applications that require deposition of thin films with precisely controlled thickness and refractive index over the active area of the element. Typically numerous substrates, each including many elements, are processed simultaneously. Thus, highly uniform deposition is required over wide areas for many applications.

For example, optical filters for applications such as optical fiber communication systems may require multiple layers of highly uniform thin films, where each layer has a precise thickness. Optical fiber communication systems are now widely deployed. Recently new communications services such as the Internet, high-speed data links, video services, and wireless services have resulted in a dramatic increase in the need for bandwidth. Data traffic is currently increasing at a rate of 80% per year and voice traffic is currently increasing at a rate of 10% per year.

One way of increasing bandwidth in optical fiber communications system is to increase the number of wavelengths of light propagating in the optical fiber. Wavelength division multiplexing (WDM) is an optical technology that propagates many wavelengths in the same optical fiber, thus effectively increasing the aggregate bandwidth per fiber to the sum of the bit rates of each wavelength. Bandwidths greater than 1 terabits/sec have been demonstrated in WDM based communication systems.

Dense Wavelength Division Multiplexing (DWDM) is a technology that implements WDM technology with a large number of wavelengths. DWDM is typically used to describe WDM technology that propagates more than 40 wavelengths in a single optical fiber. As the number of wavelengths increases, the channel width and channel spacing decreases. To achieve the required channel width and channel spacing in DWDM communication systems, high quality, high performance optical filters are required. These optical filters must exhibit low loss and narrow band transmission characteristics over the wavelength spectrum of 1.3 $\mu$m to 1.62 $\mu$m with good mechanical properties, which are stable in typically operating environments.

For example, DWDM communication systems require many band-pass filters that can separate a single wavelength (channel) from the other wavelengths (channels) propagating in the system. One type of optical filter that is used as a bandpass filter in DWDM communication systems is a Fabry Perot interference filter. Fabry Perot filters comprise two high-reflectance multi-layers separated by a $\lambda/2$ layer. In operation, multiple interferences in the $\lambda/2$ space layer cause the filter output spectral characteristic to peak sharply over a narrow band of wavelengths that are multiples of the $\lambda/2$ space layer.

Another type of optical filter used in DWDM communication systems is a dielectric thin film interference filter. These filters comprise alternative layers of high refractive index and low refractive index material. Each layer is a $\lambda/4$ thick. In operation, light reflected from high index layers does not experience a phase shift, but light reflected from the low index layers does experiences a 180 degree phase shift. Successive reflections recombine constructively at the front face producing a highly reflected beam having a narrow wavelengths range. Light having wavelengths outside of this narrow range is reflected at only very low intensity levels.

A dielectric thin film interference filter can be fabricated by depositing alternating layers of high and low refractive index material onto a glass substrate. For example, alternating layers of $SiO_2$ and $Ta_2O_5$ can be used. The refractive index and the uniformity across the filter must be controlled to a very high precision in order to achieve the desired filter characteristics.

There is presently a need for deposition systems that can deposit optical thin films with precisely controlled thickness and refractive index. Furthermore, there is a growing need for such system with the capability of depositing these optical thin films in high volume.

SUMMARY OF THE INVENTION

The present invention relates to in-situ monitoring and control of at least one of thickness and refractive index of optical thin films during deposition. In one embodiment, the present invention determines thickness and refractive index of an optical thin film in-situ from measurements of the transmission of multi-wavelength light through the optical thin film. In another embodiment, the optical thin film thickness and refractive index can be determined independent of environmental effects and of instabilities in the optical source and optical receiver by using an algorithm that normalizes the transmission of light through the optical thin film.

Accordingly, in one embodiment, the present invention features a method of determining at least one of the thickness and refractive index of an optical thin film. The method includes generating a diagnostic light beam having a first and a second wavelength. The method also includes measuring unattenuated light intensities at the first and the second wavelength of the diagnostic light beam. The method also includes measuring attenuated light intensities at the first and the second wavelength of the diagnostic light beam after transmission through an optical thin film. The method further includes measuring null light intensities at the first and the second wavelength of the diagnostic light beam after transmission through a substantially opaque material. A first and second normalized intensity function is determined using the measured unattenuated light intensities, the measured attenuated light intensities, and the measured null light intensities. At least one of the thickness and refractive index of the optical thin film is then determined by solving the first and second normalized intensity function for thickness and refractive index.

In another embodiment, the method includes solving the first and second normalized intensity function for at least one of the absolute thickness and refractive index of the optical thin film. In another embodiment, solving for at least one of the absolute thickness and refractive index of an optical thin film is performed in-situ.

The method further includes measuring the unattenuated light intensities of the diagnostic light beam by detecting the intensities of the diagnostic light beam after transmission through a substantially transparent material.

In another aspect, the method includes determining the first normalized intensity function by determining a ratio of the difference of the measured attenuated light intensity at the first wavelength and the measured null light intensity at the first wavelength to the difference of the measured unattenuated light intensity at the first wavelength and the measured null light intensity at the first wavelength. The method also includes determining the second normalized intensity function by using a ratio of the difference of the measured attenuated light intensity at the second wavelength and the measured null light intensity at the second wavelength to the difference of the measured unattenuated light intensity at the second wavelength and the measured null light intensity at the second wavelength.

In another embodiment, at least two of the measured unattenuated light intensities, the measured attenuated light intensities, and the measured null light intensities are performed substantially simultaneously in time.

In another embodiment, the invention features an apparatus for determining at least one of thickness and refractive index of an optical thin film. The apparatus includes an optical source that generates a diagnostic light beam at a first and a second wavelength. The apparatus also includes a substrate support including a first, second, and third region. Each of the first, second, and third regions are positioned to receive the diagnostic light beam and to attenuate the diagnostic light beam with a different attenuation. One of the first, second, and third regions is adapted to support a substrate having an optical film. The apparatus further includes at least one detector positioned to receive the diagnostic light beam after transmission through each of the first, second, and third regions. The at least one detector is adapted to measure the light intensity of the diagnostic light beam after transmission through the first, second, and third regions. A processor determines at least one of the thickness and refractive index of the optical thin film from a first and a second normalized intensity function. The first and the second normalized intensity function is determined from the measured light intensity of the diagnostic light beam after transmission through the first, second, and third regions.

In one embodiment, the at least one detector is a single detector. In another embodiment, the at least one detector is a plurality of detectors. In still another embodiment, the at least one detector includes a first, a second, and a third detector that each detect light intensity of the diagnostic light beam after transmission through the first, second, and third regions, respectively.

In one embodiment, the substrate support is adapted to support a plurality of substrates. In another embodiment, at least one of the first, second, and third regions includes a substantially transparent region. In still another embodiment, at least one of the first, second, and third regions includes a substantially opaque region.

In yet another embodiment, the optical source includes a laser and the detector includes a photodetector. In another embodiment, the laser is a tunable multi-wavelength laser. In still another embodiment, the apparatus includes a lock-in amplifier electrically coupled to the detector and the laser for synchronizing electrical signals received from the detector with a rotation rate of the substrate support. Another embodiment includes a bandpass filter electrically coupled to the detector.

In another embodiment, the present invention features a method of determining at least one of the thickness and refractive index of an optical thin film. The method includes generating a diagnostic light beam having a first and a second wavelength. The method also includes measuring light intensities at the first and the second wavelength of the diagnostic light beam. The method also includes measuring light intensities at the first and the second wavelength of the diagnostic light beam after transmission through an optical thin film. The method further includes measuring null light intensities at the first and the second wavelength of the diagnostic light beam. A first and second normalized intensity function is determined using the measured light intensities of the diagnostic light beams at the first and the second wavelength, the measured light intensities of the diagnostic light beams at the first and the second wavelength, and the measured null light intensities at the first and the second wavelength. At least one of the thickness and refractive index of the optical thin film is then determined by solving the first and second normalized intensity function for at least one of thickness and refractive index.

BRIEF DESCRIPTION OF THE DRAWINGS

This invention is described with particularity in the appended claims. The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
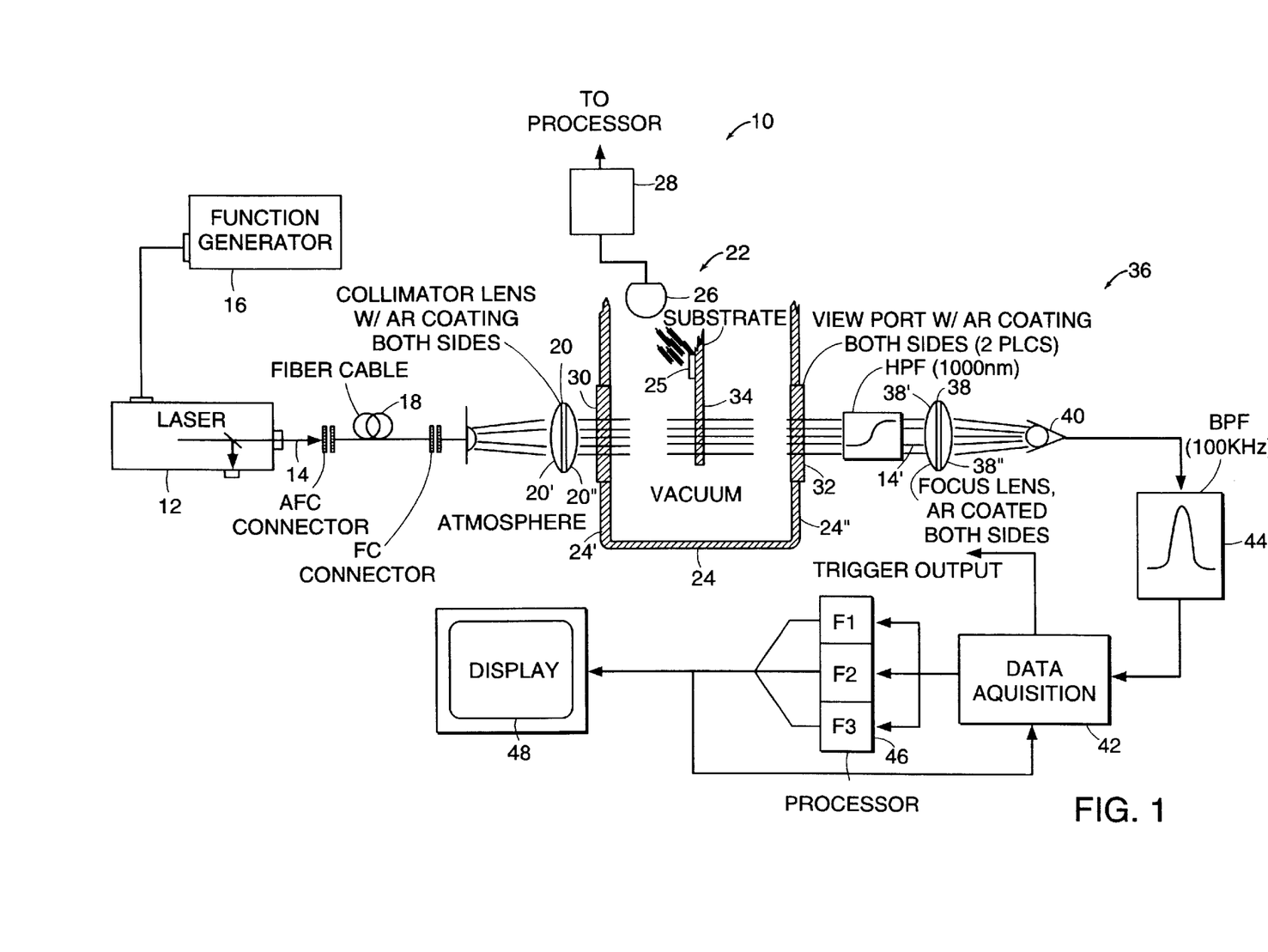
FIG. 1 illustrates a thin film deposition and monitoring system that includes an in-situ deposition rate, film thickness and refractive index monitoring system according to the present invention.

FIG. 1 illustrates a thin film deposition and monitoring system 10 that includes an in-situ deposition rate, film thickness and refractive index monitoring system according to the present invention. The system 10 includes a light source, such as a laser 12, that generates a diagnostic optical beam 14 for monitoring the deposition of the thin films. In one embodiment, the laser 12 is a tunable multi-wavelength laser.

In one embodiment, the laser 12 includes a signal or function generator 16 that is electrically connected to the laser 12 or that is integrated directly into the laser 12. In another embodiment, the system 10 includes an external modulator, such as a light modulator, that externally modulates the diagnostic optical beam 14. The function generator 16 or external modulator modulates the diagnostic optical beam 14 with a signal that can be detected after being transmitted through the substrate and thin film.

The laser 12 may be coupled to a fiber optical cable 18 that delivers the modulated diagnostic optical beam 14 to the deposition chamber. The deposition and monitoring system 10 also includes beam-shaping optics 20 that shapes the modulated diagnostic optical beam 14 so that it propagates through the thin film being monitored. In one embodiment, the beam-shaping optics 20 is anti-reflection coated on at least one of an incident 20' and a transmitted surface 20".

The deposition and monitoring system 10 includes a deposition system 22 that deposits thin films onto substrates 25. Any type of deposition system can be used. For example, the deposition system may be an evaporation system, a magnetron sputtering system, or an ion beam deposition system. In one embodiment, the deposition system includes a two-dimensional mechanical scanning system that improves deposition uniformity as described in connection with FIGS. 3 and 4. The deposition system 22 includes a vacuum chamber 24 and a deposition source 26. The deposition source 26 includes a deposition controller 28 that controls at least one of the deposition rate and the characteristics of the deposition, such as the thin film composition.

The deposition chamber 24 includes a first optical window 30 positioned on an incident surface 24' of the deposition chamber 24 and a second optical window 32 positioned on a exit surface 24" of the deposition chamber 24. These optical windows 30, 32 are substantially optical transparent to the modulated diagnostic optical beam 14. In one embodiment, the optical windows 30, 32 are anti-reflection coated to prevent the detection or erroneous signals.

A substrate support 34 that supports substrates 25 during deposition is positioned in the deposition chamber 24. The substrate support 34 may hold numerous substrates 25 for high volume batch processing. In one embodiment, the substrate support 34 includes a two-dimensional mechanical scanning system, as described in connection with FIGS. 3 and 4. The uniformity of the thin films can be increased substantially by linearly translating the substrate support 34 in one dimension and also rotating the substrate support 34.

The substrate support 34 is positioned in the path of the modulated diagnostic optical beam 14. In one embodiment, the substrate support 34 includes three Areas, I, II, and III, as described in connection with FIGS. 2A and 2B. Area I is an optically transparent area. Area II is an optically opaque area. Area III is a substrate support area that supports the substrate 25 being processed, such that the modulated diagnostic optical beam 14 passes through the substrate 25, but is not perturbed by the substrate support 34.

Thus, the substrate support 34 of the present invention transforms the modulated diagnostic optical beam 14 into three states of modulated optical diagnostic beams. The first state is when the diagnostic optical beam 14 passes through the substrate support 34 substantially unattenuated. This state represents the amplitude of the diagnostic optical beam 14 itself and can be used for calibration and compensation of the laser 12 and the optical receiver for system instabilities and any environmental changes.

The second state is when the diagnostic optical beam 14 is substantially blocked. This state represents a zero or null state that can also be used for calibration and compensation of the laser 12 and the optical receiver for system instabilities and any environmental changes. The third state is when the diagnostic optical beam 14 is transmitted through the substrate 25 and optical thin film being processed. This state represents an attenuated modulated diagnostic optical beam 14 that has an amplitude, which is proportional to the thickness and refractive index of the deposited thin film.

The deposition and monitoring system 10 also includes an optical receiver 36. The optical receiver 36 detects and processes the transmitted diagnostic optical beam 14'. In one embodiment, the optical receiver 36 comprises receiver beam shaping optics 38 that shapes the transmitted diagnostic optical beam 14' so that it can be detected and processed. The receiver beam shaping optics 38 may include a lens. The lens may have an anti-reflection coating on at least one of an incident surface 38' and an exit surface 38". The optical receiver 36 also includes a detector 40 that detects the transmitted diagnostic optical beam 14' and generates an electrical signal that characterizes the transmitted diagnostic optical beam 14'.

In one embodiment, the detector 40 includes multiple detectors that are positioned to receive the diagnostic beam. For example, the multiple detectors could include a first, second, and third detector that detect light intensity of the diagnostic light beam after transmission through the first, second, and third region, respectively.

In one embodiment, the detector 40 is positioned to receive the diagnostic optical beam 14' after transmission through the three Areas, I, II, and III of the substrate support 34 as described in connection with FIGS. 2A and 2B. In other embodiments (not shown), the detector 40 is be positioned to receive the diagnostic optical beam 14' after reflection from the three areas of the substrate support 34 or after reflection from a mirror positioned adjacent to the three areas. Skilled artisans will appreciate that there are numerous means for detecting the diagnostic optical beam 14' according to the present invention.

The optical receiver 36 also includes a data acquisition unit 42 that is electrically connected to an electrical output of the detector 40. The data acquisition unit 42 acquires the electrical signals generated by the detector 40 so that they can be stored, displayed and/or processed. In one embodiment, a lock-in amplifier or bandpass filter 44 is used to synchronize the data acquisition to the modulated laser beam and the rotation rate of the substrate support 34. The data acquisition unit 42 acquires data for three states of the transmitted diagnostic optical beam 14'.

The deposition and monitoring system 10 includes a processor 46 that processes the acquired electrical data and uses algorithms to determine deposition parameters, such as absolute thin film thickness and refractive index, as well as deposition rate and other parameters. The processor 46 may implement numeric filters and determine the absolute thin film thickness and refractive index from the filtered data. The deposition and monitoring system 10 may also include a display 48 that visually presents the acquired or processed data.

In one embodiment, an output of the processor 46 is electrically connected to the deposition controller 28 and the processor adjusts the deposition parameters in-situ. The processor 46 generates a signal that instructs the deposition controller 28 to change at least one of the deposition rate or deposition characteristics, such as the thin film composition.

In one embodiment, an algorithm processes received data from two different wavelengths of light generated by the laser 14 to determine the absolute thickness and refractive index of the deposited film. The algorithm can determine the absolute thickness and refractive index in situ so that the deposition process can be modified appropriately or terminated at the appropriate time. The transmission at the first wavelength is one function of absolute thickness and refractive index. The transmission at the second wavelength is another function of absolute thickness and refractive index. From these two equations, the two unknown, the absolute thickness and refractive index, can be determined as indicated below.

$$T_1(\lambda_1) = f_1(t,n)$$
$$T_2(\lambda_2) = f_2(t,n) \rightarrow t, n$$

Environmental effects and instabilities in the optical source and optical receiver can be compensated for by normalizing the transmission functions using absolute transmittance data for the three states of the transmitted diagnostic optical beam 14'. An example of a normalized transmission function is the ratio of the difference in the transmission in Area III (the thin film and substrate area) and the transmission in Area II (the substantially opaque area) to the difference in the transmission in Area I (the substantially transparent area) and the transmission in Area II, as shown below.

$$\text{Transmission } (t) = {}^{T(t, \text{Area III}) - T(t, \text{Area II})}/{}_{T(t, \text{Area I}) - T(t, \text{Area II})} \leq 100\%$$

Figure 2A:
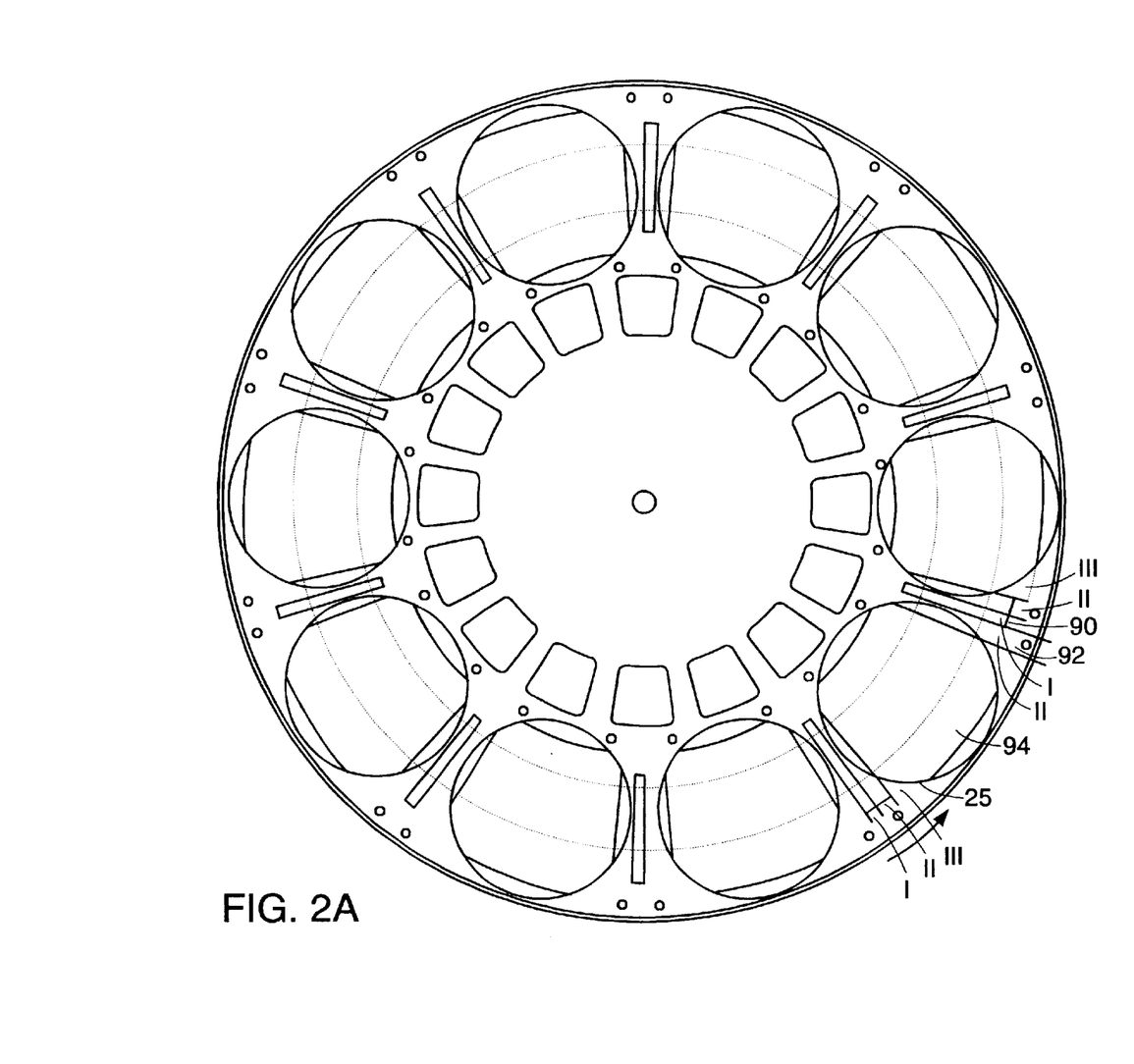
FIG. 2A illustrates an embodiment of the substrate support described in connection with FIG. 1.

FIG. 2A illustrates an embodiment of the substrate support 34 described in connection with FIG. 1. The substrate support 34 includes three areas: an optically transparent area 90 (Area I); an optically opaque area 92 (Area II); and a substrate support area 94 (Area III) that support the substrate 25 being processed such that the modulated diagnostic optical beam 14 passes through the substrate 25, but is not perturbed by the substrate support 34.

The optically transparent area 90 (Area I) may be an aperture or other opening in the substrate support 34. The optically transparent area 90 (Area I) of the substrate support 34 substantially passes the entire modulated diagnostic optical beam 14. The optically opaque area 92 (Area II) of the substrate support 34 substantially blocks the entire modulated diagnostic optical beam 14. The substrate support area 94 (Area III) of the substrate support 34 supports the substrate 25 being processed so that the modulated diagnostic optical beam 14 passes through the substrate 25 being processed in such a way that it is not perturbed by the substrate support 34.

Figure 2B:
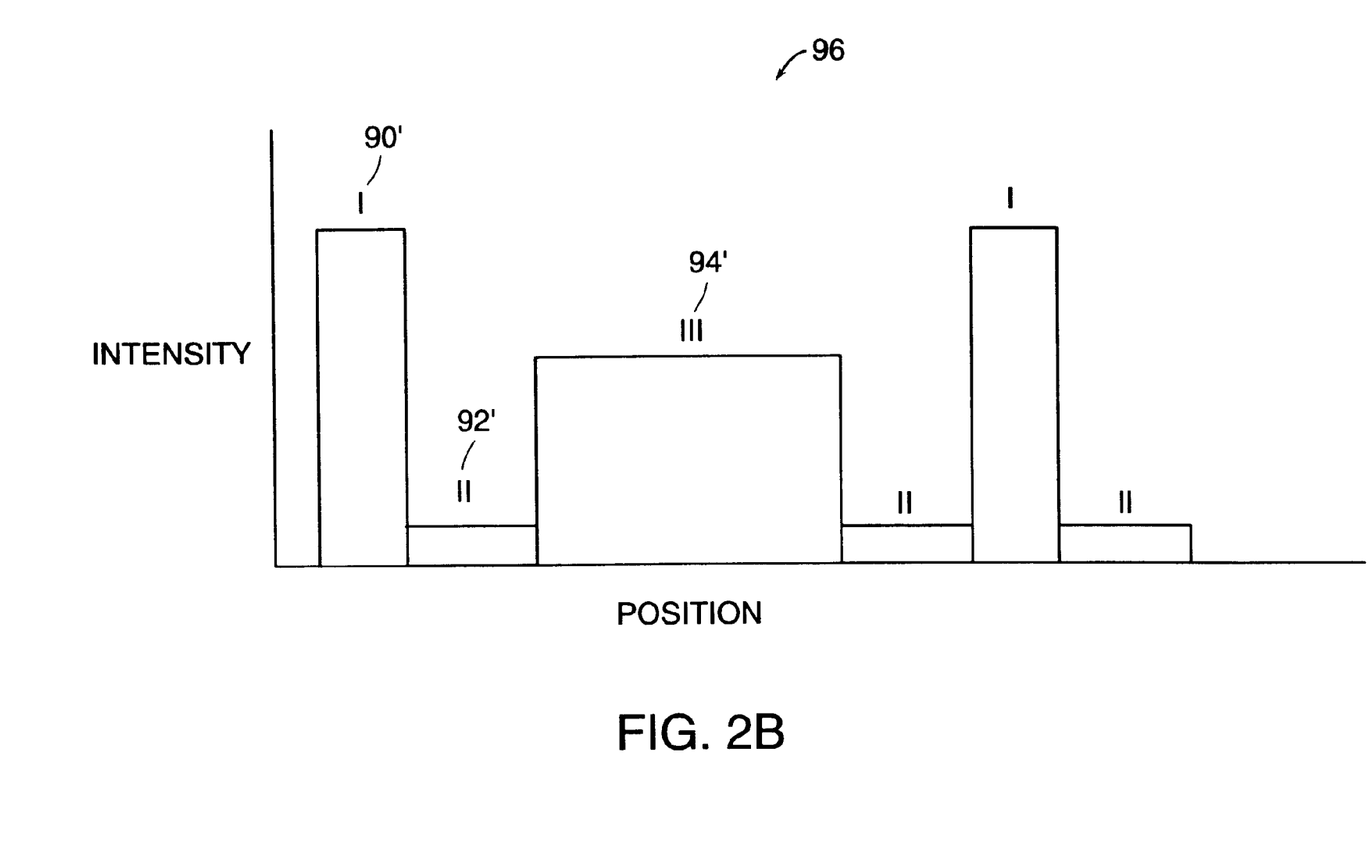
FIG. 2B illustrates an exemplary transmission pattern of a modulated diagnostic optical beam propagating through Regions I, II, and III, as described in connection with FIG. 1.

FIG. 2B illustrates an exemplary transmission pattern 96 of the modulated diagnostic optical beam propagating through Regions I, II, and III, as described in connection with FIG. 1. The transmission pattern represents detected intensity as a function of position. Intensity I 90' represents an intensity of the modulated diagnostic optical beam propagating through the substrate support 34 unperturbed by the substrate support 34. Intensity I 90' is used for compensation as described herein. Intensity II 92' represents an intensity of the modulated diagnostic optical beam that is substantially blocked from propagating through the substrate support 34. Intensity II 92' is also used for compensation as described herein.

Intensity III 94' represents an intensity of the modulated diagnostic optical beam that propagates directly through the substrate 25 and optical thin film being processed in such a way that it is not perturbed by the substrate support 34. An algorithm according to the present invention uses the intensities I 90', II 92', and III 94' to determine the absolute thickness and refractive index of the thin film being deposited independent of environmental effects and instabilities in the optical source and optical receiver, as described herein.

Figure 3:
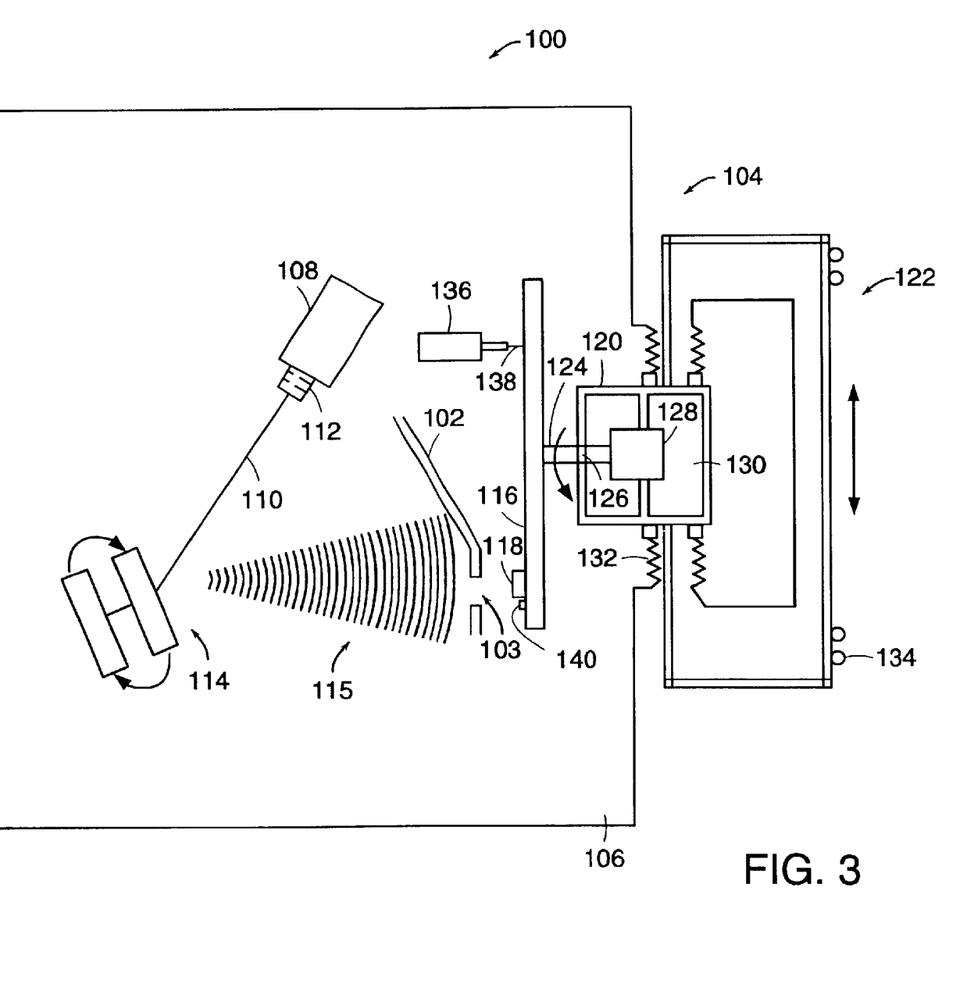
FIG. 3 illustrates a schematic diagram of an ion beam sputter deposition system that includes a shield and a two-dimensional mechanical scanning system according to the present invention.

FIG. 3 illustrates a schematic diagram of an ion beam sputter deposition system 100 that includes a shield 102 and a two-dimensional mechanical scanning system 104 according to the present invention. The system 100 includes a vacuum chamber 106. In one embodiment, the vacuum chamber 106 can achieve high vacuum in the range of less than $10^{-7}$ torr.

The system 100 includes an ion source 108 that generates an ion beam 110. In one embodiment, the system 100 includes more than one ion source. A gas, such as argon or oxygen, or a mixture of gases, is introduced into the ion source 108. A plasma is generated in the ion source 108. Ions are extracted from the plasma from two or more multi-aperture electrodes 112. The ions are then accelerated. In one embodiment, the ions are accelerated to energies in the range of 500 eV to 2000 eV.

One or more targets 114 are positioned in the path of the accelerated ion beam 110. The targets 114 may be metal or dielectric targets. The targets 114 may be formed of a single target material or may be formed of a compound target material comprising two or more materials. In some applications, dielectric thin films are formed by using metallic targets and by injecting a second gas such as oxygen or nitrogen in the ion source 108 or by directly injecting the second gas in the vacuum chamber 106.

Any target configuration can be used in the deposition system 100 of the present invention and there are numerous target configurations known in the art and commercially available. In one embodiment, the system 100 includes a rotatable target with at least two target faces. The ion beam 110 strikes the target 114 and sputters neutral atoms from the target 114 with a deposition flux 115.

The shield 102 that defines the aperture 103 is positioned in the path of the deposition flux 115. The shield 102 passes deposition flux 115 through the aperture 103 and substantially blocks the deposition flux 115 from propagating past the shield 102 everywhere else. The aperture 103 spatially defines the deposition flux 115 that reaches the substrates 118.

A substrate support 116 is positioned proximate to the aperture 103 in the path of the deposition flux 115. In one embodiment, the substrate support 116 is a disk as described in connection with FIG. 2A. The substrate support 116 holds multiple substrates 118, but may hold only one substrate in some applications. The substrate support 116 is attached to the two-dimensional mechanical scanning system 104 that moves in two dimensions at two scan rates. In one embodiment, the scan rates in the two dimensions are different and independently controllable. The scan rate may be a rotation rate or a translation rate depending upon the scan motion.

In one embodiment, the two-dimensional mechanical scanning system 104 includes a rotational 120 and a translational scanning system 122. The rotational scanning system 120 includes a shaft 124 that is rotationally attached to the substrate support 116 and positioned through a vacuum feed through 126. The shaft 124 is rotated by a motor 128 at rotation rate. In one embodiment, the motor 128 rotates the shaft 124 at rotation rate that is greater than 1000 RPMs. In one embodiment, the motor 128 is positioned inside an enclosure 130 that is attached to the vacuum chamber 106 with a bellows 132. This allows the motor 128 to translate along a surface of the vacuum chamber 106. The inside of the enclosure 130 may be maintained at atmospheric pressure.

The translational scanning system 122 includes a linear drive mechanism 134 that translates the substrate support 116 in a linear direction at a translation rate. The linear drive mechanism 134 may be attached to the substrate support 116 and may also be attached to the vacuum chamber 106. As the linear drive mechanism 134 moves, the substrate support 116 translates along with the drive mechanism 134, thereby causing the substrate support to translate relative to the aperture 103 at the translation rate.

In one embodiment, the scan speed in one dimension is much faster than the scan speed in the other direction. Using one scan speed that is much faster compared to the other scan speed reduces ripples in the thickness uniformity. By much faster, we mean that one scan speed is greater than five-time faster than the other scan speed. In one embodiment of the ion beam sputter deposition system 100 of FIG. 3, the rotation rate is much faster than the linear translation rate.

In one embodiment, the scan speed in at least one dimension varies during the deposition. For example, in one embodiment, the scan speed in one dimension is varied in order to improve uniformity. The deposition flux 115 is a function of the radial position from the center of the aperture 103 and, therefore, there is a radial uniformity effect. The radial uniformity effect can be at least partially compensated by varying the linear translation rate. In one embodiment, a constant 1/R correction is applied to the linear translation rate.

There are numerous other embodiments of the two-dimensional mechanical scanning system 104 of the present invention. In other embodiments, the aperture 103 and/or the target 114 are scanned in at least one dimension. Any combination of scanning the substrate support 116, the aperture 103, and/or the target 114 in at least two dimensions will improve the uniformity according to the present invention. For example, in one embodiment, the substrate support 116 is stationary and the aperture 103 and/or target 114 are scanned in two dimensions. In another embodiment, the substrate support 116 is scanned in one dimension and the aperture 103 and/or target 114 are scanned in one dimension.

In one embodiment, the ion beam sputter deposition system 100 includes a second ion source 136 that generates a second ion beam 138 used for ion beam assisted deposition. The second ion source 136 is positioned so that the second ion beam 138 strikes the substrate in the region that is exposed to the deposition flux 115. In the embodiment shown in FIG. 3, the substrate support 116 comprises a rotating disk. One end of the rotating disk is positioned adjacent to the aperture 103 that passes the deposition flux 115. The other end of the rotating disk is positioned in the path of the second ion beam 138. The radial distance to the aperture 103 is approximately the same as the radial distance to the path of the second ion beam 138. The second ion beam 138 can be used to improve adhesion of the thin film to the substrate 118 or it can be used to change the properties of the thin film during deposition.

In one embodiment, the ion beam sputter deposition system 100 includes an ion detector 140 that monitors the deposition flux 115. The ion detector 140 may be a quartz oscillator that measures thin film thickness and/or deposition rate. In one embodiment, the shield 102 includes a second aperture (not shown) that passes a portion of the deposition flux 115. The ion detector 140 is positioned behind the aperture to detect and measure the deposition flux 115. The measurement of the deposition flux 115 can be used to change the parameters of the ion source 108 for various applications including generating a more uniform ion beam. In addition, the measurement of the deposition flux 115 can be used to control the rotation rate of the rotational scanning system 120 and/or the translation rate of the translational scanning system 122.

Figure 4:
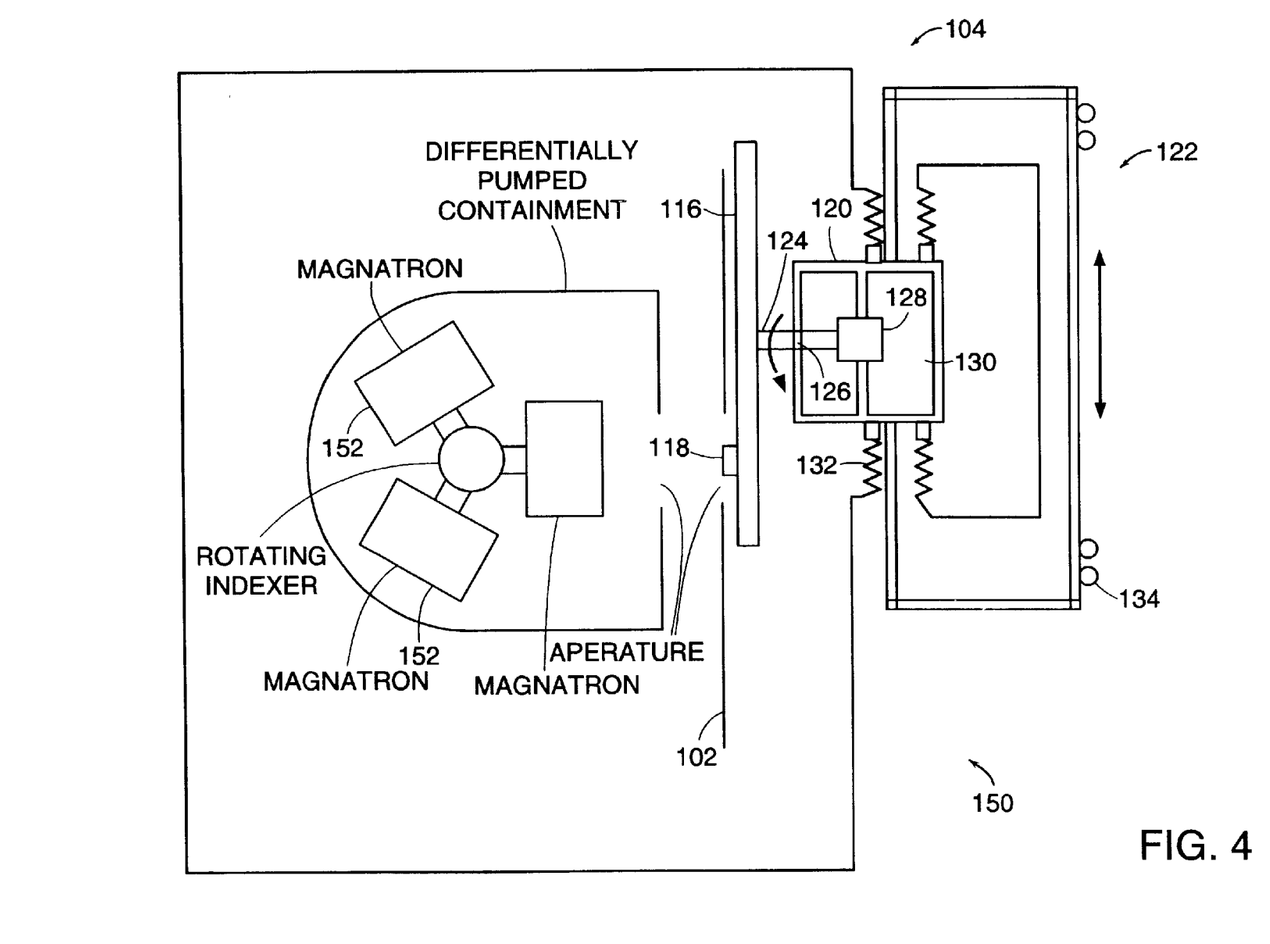
FIG. 4 illustrates a schematic diagram of a magnetron sputter deposition system that includes a shield and a two-dimensional mechanical scanning system according to the present invention.

FIG. 4 illustrates a schematic diagram of a magnetron sputter deposition system 150 that includes a shield 102 and a two-dimensional mechanical scanning system 104 according to the present invention. The magnetron system 150 is similar to the ion beam sputter deposition system 100 of FIG. 3. However, a magnetron sputtering source 152 generates the deposition flux 115.

In one embodiment, the magnetron sputtering system 150 includes differential pumping. The magnetron sputtering source 152 is pumped to one pressure and the substrate support 116 is pumped to another pressure, which is typically a lower pressure. The differentially pumped magnetron sputtering deposition system 150 has several advantages over prior art magnetron sputtering systems. One advantage is that sputtered films deposited by such systems can have higher purity because they are deposited at lower pressure.

There are numerous other embodiments of deposition systems according to the present invention that include a beam aperture and/or a two-dimensional scanning system that improves deposition uniformity. For example, one embodiment uses an electron beam evaporation source that generates the deposition flux 115. This embodiment is similar to the ion beam sputter deposition system 100 of FIG. 3 and the magnetron system 150 described in connection with FIG. 4.

Equivalents

While the invention has been particularly shown and described with reference to specific preferred embodiments, it should be understood by those skilled in the art that various changes in form and detail may be made therein without departing from the spirit and scope of the invention as defined by the appended claims. For example, the present invention can be applied to any type of thin film deposition system.

What is claimed is:

1. A method of determining at least one of thickness and refractive index of an optical thin film, the method comprising:
   a) generating a diagnostic light beam having a first and a second wavelength;
   b) measuring unattenuated light intensities at the first and the second wavelength of the diagnostic light beam;
   c) measuring attenuated light intensities at the first and the second wavelength of the diagnostic light beam after transmission through the optical thin film;
   d) measuring null light intensities at the first and the second wavelength of the diagnostic light beam after the diagnostic light beam is blocked by an optically opaque material;
   e) determining a first and a second normalized intensity function from the measured unattenuated light intensities, the measured attenuated light intensities, and the measured null light intensities; and
   f) solving the first and the second normalized intensity function for at least one of thickness and refractive index of the optical thin film.

2. The method of claim 1 wherein the solving the first and second normalized intensity function for at least one of thickness and refractive index comprises solving for at least one of the absolute thickness and refractive index of the optical thin film.

3. The method of claim 1 wherein the solving the first and second normalized intensity function for at least one of thickness and refractive index is performed in-situ.

4. The method of claim 1 wherein the measuring unattenuated light intensities at the first and the second wavelength of the diagnostic light beam comprises detecting the intensities of the diagnostic light beam after transmission through a substantially transparent material.

5. The method of claim 1 wherein the determining of the first normalized intensity function comprises determining a ratio of the difference of the measured attenuated light intensity at the first wavelength and the measured null light intensity at the first wavelength to the difference of the measured unattenuated light intensity at the first wavelength and the measured null light intensity at the first wavelength.

6. The method of claim 1 wherein the determining of the second normalized intensity function comprises determining a ratio of the difference of the measured attenuated light intensity at the second wavelength and the measured null light intensity at the second wavelength to the difference of the measured unattenuated light intensity at the second wavelength and the measured null light intensity at the second wavelength.

7. The method of claim 1 wherein at least two of the measuring unattenuated light intensities, measuring attenuated light intensities, and the measuring null light intensities are performed substantially simultaneously in time.

8. An apparatus for determining at least one of thickness and refractive index of an optical thin film, the apparatus comprising:
   a) an optical source that generates a diagnostic light beam having a first and a second wavelength;
   b) a substrate support including a first, second, and third region, each of the first, second, and third regions being positioned to receive the diagnostic light beam and being adapted to attenuate the diagnostic light beam with a different attenuation, and one of the first, second, and third regions being adapted to support a substrate having an optical thin film;
   c) at least one detector positioned to receive the diagnostic light beam after transmission through each of the first, second, and third regions, the at least one detector adapted to measure light intensity of the diagnostic light beam after transmission through the first, second, and third regions; and
   d) a processor that determines at least one of the thickness and the refractive index of the optical thin film by solving a first and a second normalized intensity function for at least one of thickness and refractive index, the first and the second normalized intensity function being determined from the measured light intensity of the diagnostic light beam after transmission through the first, second and third regions.

9. The apparatus of claim 8 wherein the at least one detector comprises a single detector.

10. The apparatus of claim 8 wherein the at least one detector comprises a first, second, and third detector that detect light intensity of the diagnostic light beam after transmission through the first, second, and third region, respectively.

11. The apparatus of claim 8 wherein the substrate support is adapted to support a plurality of substrates.

12. The apparatus of claim 8 wherein at least one of the first, second, and third region comprises a substantially transparent region.

13. The apparatus of claim 8 wherein at least one of the first, second, and third region comprises an optically opaque region.

14. The apparatus of claim 8 wherein the optical source comprises a laser.

15. The apparatus of claim 14 wherein the laser comprises a tunable multi-wavelength laser.

16. The apparatus of claim 8 wherein the detector comprises a photodetector.

17. The apparatus of claim 8 further comprising a lock-in amplifier that is electrically coupled to the at least one detector, the lock-in amplifier synchronizing electrical signals received from the at least to one detector with the optical source and a position of each of the first, second and third regions.

18. A method of measuring at least one of thickness and refractive index of an optical thin film, the method comprising:
   a) generating a diagnostic light beam having a first and a second wavelength;
   b) measuring light intensities at the first and the second wavelength of the diagnostic light beam;
   c) measuring light intensities at the first and the second wavelength of the diagnostic light beam after transmission through the optical thin film;
   d) measuring null light intensities at the first and the second wavelength of the diagnostic light beam;
   e) determining a first and a second normalized intensity function from the measured light intensities of the diagnostic light beam at the first and the second wavelength, the measured light intensities of the diagnostic light beam at the first and the second wavelength after transmission through the optical thin film and the measured null light intensities of the diagnostic light beam at the first and second wavelength; and
   f) determining at least one of the thickness and the refractive index of the optical thin film by solving the first and second normalized intensity function for at least one of thickness and refractive index.

19. The method of claim 18 wherein the determining at least one of the thickness and the refractive index of an optical thin film is performed in-situ.

20. The method of claim 18 wherein at least two of the measuring light intensities, the measuring light intensities after transmission, and the measuring null light intensities are performed substantially simultaneously in time.

21. The method of claim 1 further comprising modulating the diagnostic light beam with a signal to generate a modulated diagnostic light beam having the first and the second wavelengths.

22. The method of claim 18 further comprising modulating the diagnostic light beam with a signal to generate a modulated diagnostic light beam having the first and the second wavelengths.

23. A deposition system comprising:
   a) a deposition source tat deposits an optical thin film on a substrate;
   b) an optical source that generates a diagnostic light beam having a first and a second wavelength;
   c) a substrate support including a first, second, and third region, each of the first, second, and third regions being positioned to receive the diagnostic light beam and being adapted to attenuate the diagnostic light beam with a different attenuation, and one of the first, second, and third regions being adapted to support the substrate;
   d) at least one detector positioned to receive the diagnostic light beam after transmission through each of the first, second, and third regions, the at least one detector adapted to measure light intensity of the diagnostic light beam after transmission through the first, second, and third regions;

e) a processor that generates a signal by solving a first and a second normalized intensity function for at least one of thickness and refractive index, the fast and the second normalized intensity function being determined from the measured light intensity of the diagnostic light beam after transmission through the first, second, and third regions; and f) a deposition controller that is electrically connected to the processor and to the deposition source, the deposition controller adjusting at least one deposition parameter of the deposition source in response to the signal generated by the processor to control the at least one of thickness and refractive index of the optical thin film on the substrate.

24. The deposition system of claim 23 wherein the deposition system is chosen from the group comprising an evaporation system, a magnetron sputtering system, and an ion beam deposition system.

25. The deposition system of claim 23 further comprising a modulator that is coupled to the optical source, the modulator modulating the diagnostic light beam with a signal to generate a modulated diagnostic light beam having the first and the second wavelengths.

26. The deposition system of claim 23 wherein the at least one deposition parameter comprises a deposition rate.

27. The deposition system of claim 23 wherein the at least one deposition parameter comprises a thin film composition.

28. The deposition system of claim 23 wherein the processor determines the at least one of the thickness and the refractive index of the optical thin film in-situ.

29. The deposition system of claim 23 wherein the deposition controller changes the at least one deposition parameter in-situ.

* * * * *